United States Patent [19]
Stoss et al.

[11] 3,992,376
[45] Nov. 16, 1976

[54] PHENOTHIAZINE SULPHOXIMIDES

[75] Inventors: Peter Stoss, Wildtal; Gerhard Satzinger, Denzlingen; Manfred Herrmann, St. Peter, all of Germany

[73] Assignee: Warner-Lambert Company, Morris Plains, N.J.

[22] Filed: Aug. 12, 1974

[21] Appl. No.: 496,618

[30] Foreign Application Priority Data
Apr. 8, 1974  Germany............................ 2417063

[52] U.S. Cl. ............................ 260/243 A; 424/247; 424/275; 424/276; 424/277; 260/293.57; 260/326.34; 260/326.83; 260/327 B; 260/327 P; 260/328; 260/329.3
[51] Int. Cl.² ........................................ C07D 279/10
[58] Field of Search ................................ 260/243 A

[56] References Cited
OTHER PUBLICATIONS

Tamura et al., "Tetrahedron Letters", No. 40, pp. 4137–4140, (1972).
Stoss et al., "Tetrahedron Letters", No. 23, pp. 1973–1976, (1974).

*Primary Examiner*—Henry R. Giles
*Assistant Examiner*—R. W. Ramsuer
*Attorney, Agent, or Firm*—Albert H. Graddis; Frank S. Chow; George M. Yahwak

[57] ABSTRACT

The present invention is concerned with novel tricyclic sulphoximides and with the preparation thereof. This family of compounds has been found to possess antihistaminic, antitussive, antiinflammatory, sedative, and diuretic properties.

11 Claims, No Drawings

PHENOTHIAZINE SULPHOXIMIDES

The cyclic sulphoximides have not been hitherto investigated to any great extent. For this reason, very little is known about the pharmacological effectiveness of these compounds. We have found however the aromatic compounds of this type to be of interest because of their potential physiological effectiveness.

More particularly, we have found that the new compounds of this clinical family possess an antitussive, antihistaminic, antiphlogistic, sedative and diuretic effectiveness.

We have now found that the tricyclic sulphoximide family of the general formula:

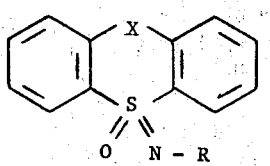   I wherein X is a valency bond, a sulphur or oxygen atom, an unsubstituted or substituted imino group, or a carbonyl group, a lower alkylene radical which can be interrupted by an oxygen or sulphur atom or by a carbonyl group or by an unsubstituted or substituted imino group; R is an optionally N-alkylated or N-acylated amino-alkyl, aminoalkylcarbonyl, alkoxycarbonyl, aminocarbonyl or aminothiocarbonyl radical possess these valuable pharmacological properties. The pharmaceutically acceptable salts of these compounds of course also possess these properties.

Lower alkylene radicals according to the present invention are preferably methylene and ethylene radicals and the oxa, thia and aza analogues thereof which, as substituents, can include lower hydrocarbon radicals. Thus X can be, for example, an ethylidene, propylidene, isobutylidene, propylene, 1,2-butylene or 1,2-isobutyl-idene radical, one ring carbon atom of which can be replaced by an oxygen or sulphur atom or by a carbonyl group or by an unsubstituted or substituted imino group. By a substituted imino group, there is to be understood an imino group which is substituted by an alkyl radical containing up to 4 carbon atoms, for example, by a methyl, ethyl, isopropyl, n-butyl or isobutyl radical, or by an acyl radical containing up to 4 carbon atoms, for example, an acetyl, propionyl or butyryl radical.

The above-given general formula I thus includes the following tricyclic systems: dibenzothiophene-S-oximide, thiaxanthene-S-oximide, thiaxanthone-S-oximide, phenoxathiine-S-oximide, thianthrene-S-oximide, phenothiazine-S-oximide, dibenzo[b,f]thiepine-S-oximide, 10, 11-dihydrodibenzo[b,f]thiepine-S-oximide, 10, 11-dihydrobenzo[b,f]thiepine-10-one-S-oximide, dibenzo[b,e]-1,4-oxa-thiepine-S-oximide, dibenzo[b,e]dithiepine-S-oximide, 10, 11-dihydrodibenzo[b,f]-1,4-thiazepine-S-oximide and dibenzo[b,f]-1,4-thiazepine-S-oximide.

The aminoalkyl radical R can be, for example, a tertiary amino group, which can be open-chained or cyclic, attached through a lower alkylene radical to the nitrogen atom of the sulphoximide group. Preferred radicals are those of the general formula:

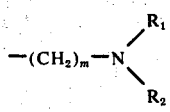   II wherein m is 1, 2, 3 or 4 and $R_1$ and $R_2$, which can be the same or different, are saturated or unsaturated aliphatic hydrocarbon radicals containing up to 7 carbon atoms; $R_1$ and $R_2$ together may also represent an alkylene chain containing 4 to 6 carbon atoms.

The aminoalkylcarbonyl radical R can be a tertiary amine radical, which is open-chained or cyclic, the nitrogen atom of which is connected, through a lower alkyl-carbonyl radical containing 2 to 4 carbon atoms, to the nitrogen atom of the sulphoximine group. Preferred radicals are those of the general formula:

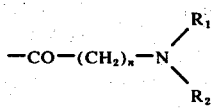   III wherein $R_1$ and $R_2$ have the same meanings as above and n is 1, 2, or 3.

The alkoxycarbonyl radical R can be, for example, one of the general formula:

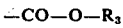   IV wherein $R_3$ is an alkyl radical containing up to 4 carbon atoms and is preferably an ethyl radical.

The aminocarbonyl or aminothiocarbonyl radical R can be, for example, one of the general formula:

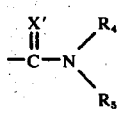   V wherein X' is an oxygen or sulphur atom and $R_4$ and $R_5$, which can be the same or different, are hydrogen atoms or saturated or unsaturated aliphatic hydrocarbon radicals containing up to 6 carbon atoms.

Furthermore, if the radical R contains a primary or secondary amino group, this group can be acylated by alkanoyl radicals containing 2 to 4 carbon atoms, for example, acetyl or propionyl radicals, or by sulphonyl radicals, for example benzene-sulphonyl or tosyl radicals.

The radicals $R_1$ and $R_2$ are preferably methyl, ethyl, propyl, butyl, hexyl, vinyl, propenyl, allyl or butenyl radicals; or $R_1$ and $R_2$, together with the nitrogen atom to which they are attached, preferably represent a pyrrolidino, piperidino or perhydroazepino radical.

The compounds of general formula I can be prepared from new tricyclic sulphoximides of the general formula:

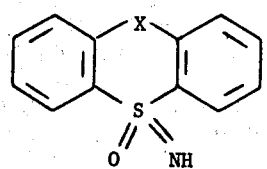   VI wherein X has the same meaning as above, or from an alkali metal or alkaline earth metal salt thereof by the following process: when R is to be an aminoalkyl radical, by reaction with an appropriate alkyl halide, especially with a compound of the general formula:

METHOD A $$\text{Hal}-(CH_2)_m-N\begin{matrix}R_1\\ \\R_2\end{matrix} \qquad VII$$

wherein $m$, $R_1$ and $R_2$ have the same meanings as above and Hal is a halogen atom, preferably a chlorine or bromine atom; when R is to be an aminoalkylcarbonyl radical, by reaction with a reactive derivative of an appropriate acid, especially with a reactive derivative of an acid of the general formula:

METHOD B $$\overset{O}{\underset{\|}{HO-C}}-(CH_2)_n-N\begin{matrix}R_1\\ \\R_2\end{matrix} \qquad VIII$$

wherein $n$, $R_1$ and $R_2$ have the same meanings as above; when R is to be an alkoxycarbonyl radical, by reaction with a halocarbonic acid ester of the general formula:

METHOD C $$\text{Hal}-CO-O-R_3 \qquad IX$$

wherein Hal and $R_3$ have the same meanings as above; and when R is to be an aminocarbonyl or aminothiocarbonyl radical, by reaction with a corresponding isocyanate or isothiocyanate or with a free acid of the general formula:

METHOD D $$X'=C=N-R_4 \qquad X$$

wherein $R_4$ and $X'$ have the same meanings as above, or with a reactive derivative of the corresponding carbamic acid of the general formula:

$$\overset{X'}{\underset{\|}{HO-C}}-N\begin{matrix}R_4\\ \\R_5\end{matrix} \qquad XI$$

wherein $X'$, $R_4$ and $R_5$ have the same meanings as above.

As reactive derivatives of acide used according to method "B", there can be used, for example, acid halides, acid anhydrides or acid imidazolides. This reaction depends upon the reactivity of the starting materials employed. In most cases, the variant described hereinafter is preferred. As reactive carbamic acid derivatives used according to method "D", there can be used, for example, a carbamic acid in the form of a halide, especially of a chloride.

Reaction "B" can also be carried out by first reacting a compound (VI) with a dihalide of the general formula:

$$\overset{O}{\underset{\|}{\text{Hal}-C}}-(CH_2)_n-\text{Hal} \qquad XII$$

wherein Hal, and $n$ have the same meanings as above, followed by reaction with an amine of the general formula:

$$R_1-NH-R_2 \qquad XIII$$

wherein $R_1$ and $R_2$ have the same meanings as above.

The compounds of general formula (VI) used as starting materials are novel and encompassed by this invention because it provides new tricyclic sulfoximides with a functional imino group. The compounds of general formula (VI) are capable of a large variety of chemical reactions via the hitherto unknown S-iminofunction in a tricyclic system according to formula (VI). They, therefore, constitute valuable new intermediates for pharmaceuticals. They can be prepared, for example, by reacting a sulphimide of the general formula:

Reaction a.)

[structure XIV: tricyclic ring system with X bridge and S=NH]

XIV wherein X has the same meaning as above, or a salt thereof with an oxidation agent, or by reacting a sulphoxide of the general formula:

Reaction b.)

[structure XV: tricyclic ring system with X bridge and S=O]

XV wherein X has the same meaning as above, either with a sulphonyl-azide of the general formula:

$$Ar-SO_2-N_3 \qquad XVI$$

wherein Ar is an unsubstituted or substituted phenyl radical, with the addition of copper powder as catalyst, in methanol; or with O-mesitylene-sulphonyl-hydroxylamine in an inert solvent; whereafter, if desired, any N-arylsulphonyl radicals present and any N-acyl radicals on the substituent X can be split off hydrolytically, and the free bases converted into salts by reaction with inorganic or organic acids.

As oxidation agents for the sulphimides of general formula (XIV), there can be used, sodium periodate, hydrogen peroxide, lead tetraacetate or potassium permanganate. The reaction can be carried out in an appropriate solvent or solvent mixture, depending upon the nature of the oxidation agent used. Examples of such solvents include glacial acetic acid, water, pyridine, chloroform, dichloromethane, dichloroethane, dioxan, acetone or a lower alcohol. The reaction is preferably carried out at ambient temperature with the use of a molar amount or of an excess of oxidation agent.

The course of the oxidation reaction "a" is surprising and was not to have been foreseen. The oxidation of N-unsubstituted sulphimides is previously only described for dimethyl sulphimide (see Chem. Ber., 95, 855/1962), whereas the oxidation of aromatic substituted sulphimides to the corresponding sulphoximides has hitherto not been described. Surprisingly, however, the compounds of general formula (XIV) can be oxidised without difficulty to compounds of general formula (VI). In this case, the desired result is obtained not only with the use of potassium permanganate, as described in the literature for examples of the aliphatic series, but also with much weaker oxidation agents (see J.A.C.S., 94, 208/1972; Tetrahedron, 27, 341/1971).

The compounds of general formulae (VI) and (XIV) form crystalline addition salts not only with inorganic acids but also with organic acids, for example, hydrochloric acid, hydrobromic acid, hydrofluoric acid, sulphuric acid, orthophosphoric acid, metaphosphoric acid, nitric acid, chloric acid, perchloric acid, sulphonic acid, oxalic acids, acetic acid, formic acid, succinic acid, citric acid, fumaric acid, lactic acid and the like.

The sulphimides of general formula (XIV) and the salts thereof are also new. They can be prepared, for example, by reacting sulphides of the general formula:

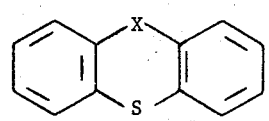

XVII wherein X has the same meaning as above, with mesitylene-sulphonyl-hydroxylamine in an inert solvent. The initially formed mesitylene-sulphonates can, if desired, be converted in known manner into the bases (XIV). Salts with inorganic or organic acids can, if desired, be prepared in the usual manner from these bases.

As inert solvent, there can be used a chlorinated hydrocarbon, such as dichloromethane or chloroform. The mesitylene-sulphonyl-hydroxylamine can be added in solid form or as a solution and the reaction can be carried out at a temperature of between about 0° C. and 30° C. over the course of 2 to 48 hours. The mesitylene-sulphonates of the compounds (XIV) usually precipitate out and can be separated off directly. In some cases, however, it is necessary to promote the precipitation by the addition of ether or of petroleum ether.

The compounds of general formula (XV) are either known or can be prepared in known manner from the corresponding sulphides. The reaction with the compounds of general formula (XVI) preferably takes place in a lower alcohol, for example methanol, ethanol or isopropanol, at the boiling point of the solvent. The reaction time is about 6 to 24 hours.

The aryl radical of the compounds (XVI) can be substituted by halogen atoms or by lower alkyl radicals, p-toluene-sulphonyl azide, p-chlorobenzene-sulphonyl azide or p-bromobenzene-sulphonyl azide preferably being used.

The copper powder used as catalyst should be as finely divided as possible. It is preferably used in 0.2 to 0.5 times the amount in grams of the amount of azide used.

The reaction of the compounds (XV) with O-mesitylene-sulphonyl-hydroxylamine is carried out in a manner analogous to that described for compounds of general formula (XVII).

If the imino group of the sulphoximide group is, after the reaction of the compounds (XV), substituted by an arylsulphonyl radical, this can be split off by hydrolysis with a strong acid, preferably concentrated sulphuric acid. The saponification requires temperatures of between 0° and 100° C. and, depending upon the reactivity, a reaction time of from 5 minutes to 24 hours. The reaction mixture is subsequently poured into water, rendered alkaline with a base, for example with an aqueous solution of sodium or potassium hydroxide or of ammonia and then extracted with an appropriate solvent, for example dichloromethane, chloroform or the like. The free base (VI) obtained after distilling off the solvent can then, if desired, be recrystallized and converted into a salt by reaction with an appropriate acid, preferably with hydrogen chloride.

The splitting off of any N-acyl radicals which may be present can be carried out even under quite mild conditions, for example, by hydrolysis in dilute hydrochloric acid or by means of an alcoholic solution of potassium hydroxide.

The following examples are given for the purpose of illustrating the formation of the novel family of compounds encompassed by general formula VI:

EXAMPLE 1

Thianthrene-S-oximide

Thianthrene-S-imide mesitylene sulphonate is prepared in the following manner:

A solution of 90 g. thianthrene in 1.6 liters methylene chloride is mixed at ambient temperature with 100 g. mesitylene sulphonyl hydroxylamine. The reaction mixture is left to stand for 48 hours and the thianthrene-S-imide mesitylene sulpnonate formed is then precipitated out with ether. The yield is 79% of theory. After recrystallization from ethyl acetate/diisopropyl ether, the compound has a melting point of 156° C.

The free base, obtained from alkaline solution, can be recrystallized from ethyl acetate and has a melting point of 153° C.

30 g. thianthrene-S-imide mesitylene sulpnonate are dissolved in 580 ml. glacial acetic acid and mixed at ambient temperature with a solution of 45 g. sodium periodate in 300 ml. water. The reaction mixture is stirred for 24 hours at ambient temperature, then poured on to ice, rendered alkaline with an aqueous solution of sodium hydroxide and subsequently extracted with methylene chloride. After stripping off the solvent, the residue obtained is recrystallized from ethyl acetate. Thianthrene-S-oximide is thus obtained in the form of colorless crystals which contain 0.75 mol water of crystallization. The yield is 55% of theory and the product melts at 193° C.

EXAMPLE 2

10-Methyl-phenothiazine-S-oximide 10-methyl-phenothiazine-S-imide is prepared in the following manner:

To a solution of 18.1 g. 10-methyl-phenothiazine in 250 ml. methylene chloride, there is added dropwise, while stirring and cooling, a solution of 18.3 g. mesitylene sulphonyl hydroxylamine in 50 ml. methylene chloride. After a short time, the 10-methyl-phenothiazine-S-imide mesitylene sulphonate precipitates out. It is filtered off with suction and recrystallized from isopropanol, whereafter it has a melting point of 169°–170° C; yield 83% of theory.

The free base obtained from alkaline solution can be recrystallized from methanol and has a melting point of 114°–115° C.

12.6 g. 10-methyl-phenothiazine-S-imide are dissolved in 110 ml. glacial acetic acid and mixed dropwise with a solution of 23.4 g. sodium periodate in 100 cc. water. The reaction mixture is then stirred for 16 hours at ambient temperature. After evaporation in a vacuum, the residue obtained is mixed with water, rendered alkaline with an aqueous solution of potassium hydroxide, extracted with methylene chloride and the extract evaporated to dryness. The residue obtained is recrystallized from isopropanol. There is obtained 10-methyl-phenothiazine-S-oximide in a yield of 42% of theory; m.p. 174°–175° C.

EXAMPLE 3

10-Acetyl-phenothiazine-S-oximide

10-Acetyl-phenothiazine-S-imide mesitylene sulphonate is prepared as follows:

120.6 g. 10-acetyl-phenothiazine in 1.3 liters methylene chloride are mixed with a solution of 107.6 g. mesitylene sulphonyl hydroxylamine in a little methylene chloride and stirred for 18 hours at ambient temperature. The reaction mixture is then cooled to 0° C. and the precipitate formed is filtered off with suction. There is obtained 10-acetyl-phenothiazine-S-imide mesitylene sulphonate in a yield of 55% of theory; m.p. 189° C.

The free base obtained from alkaline solution is recrystallized from ethyl acetate and then melts at 139°–140° C.

118.5 g. 10-acetyl-phenothiazine-S-imide mesitylene sulphonate in 400 ml. glacial acetic acid are oxidised with 110 g. sodium periodate in 200 ml. water over the course of 20 hours at ambient temperature. After evaporation of the reaction mixture in a vacuum, the residue is mixed with water, rendered alkaline with an aqueous solution of sodium hydroxide and extracted with methylene chloride. The extract is evaporated and the residue obtained is recrystallized from ethyl acetate. There is obtained 10-acetyl-phenothiazine-S-oximide in a yield of 45% of theory; m.p. 153°–154° C.

EXAMPLE 4

Phenothiazine-S-oximide 1.3 g. of the 10-acetyl-phenothiazine-S-oximide prepared in the manner described in Example 3 are heated for 1 hour at 50° C. with 0.56 g. potassium hydroxide in 50 ml. ethanol. Thereafter, the reaction mixture is mixed with water and the precipitate obtained is filtered off with suction. There is thus obtained phenothiazine-S-oximide in a yield of 77 of theory. After recrystallization from methanol, the compound has a melting point of 279°–280° C.

EXAMPLE 5

Dibenzothiophene-S-oximide

VARIANT A

A solution of 19 g. dibenzothiophene-S-oxide in 1 liter methanol is mixed, under a protective atmosphere of nitrogen, with 20 g. p-toluenesulphonyl azide and 6 g. copper powder. The reaction mixture is heated under reflux for a total time of 20 hours, whereby, after 4, 8 and 12 hours, 2 g. copper powder and 5 g. of the tosyl azide are added. Thereafter, the reaction mixture is filtered while still hot to separate off the precipitate, which is thoroughly washed with hot acetone. The filtrate is concentrated to about one third of its initial volume, the reaction product thereby separating out in the form of a crystalline precipitate. This is filtered off with suction and recrystallized from ethanol. There is obtained N-(p-toluene-sulphonyl)-dibenzothiophene-S-oximide in a yield of 62% of theory; m.p. 175° C.

7 g. of the tosylate thus obtained are heated in 5 ml. concentrated sulphuric acid for 5 minutes on a steambath and thereafter poured into ice water. The reaction mixture is rendered alkaline, while cooling, extracted with methylene chloride and the organic phase dried and then evaporated. The residue obtained is recrystallized from methanol. There is obtained pure dibenzothiophene-S-oximide; m.p. 171° C. The saponification step takes place with a yield of 85% of theory.

VARIANT B 74 g. dibenzothiophene-S-oxide are dissolved in 1 liter methylene chloride and mixed, while cooling with ice, with a solution of 86.2 g. mesitylene-sulphonylhydroxylamine in a little methylene chloride. The reaction mixture is stirred for 20 hours at ambient temperature and the precipitate formed then filtered off with suction. After recrystallization thereof from methanol, dibenzothiophene-S-oximide mesitylene-sulphonate it obtained in a yield of 40% of theory; m.p. 196°–197° C. This salt is dissolved in methanol and mixed with a molar amount of sodium methylate, water is subsequently added thereto and the precipitate formed is filtered off with suction and recrystallized from methanol. There is thus obtained pure dibenzothiophene-S-oximide; m.p. 171° C.

EXAMPLE 6

Thioxanthene-S-oximide 16 g. thioxanthene-S-oxide, 20 g. p-tosyl-azide and 6 g. copper powder are reacted and worked up in a manner analogous to that described in Example 5, Variant A. The residue of the N-p-toluene-sulphonyl-thioxanthene-S-oximide (m.p. 220° C.; yield 48% of theory) obtained as intermediate can be recrystallized from acetonitrile. After saponification with concentrated sulphuric acid and recrystallization from isopropanol, there is obtained pure thioxanthene-S-oximide, m.p. 174° C. The yield from the saponification step is 79% of theory.

EXAMPLE 7

Thioxanthone-S-oximide 10.7 g. thioxanthone-S-oxide in 600 ml. methanol are reacted in 600 ml. methanol, in the manner described in Example 5, Variant A, with 11 g. 4-chlorobenzene-sulphonyl azide and 4.5 g. copper powder and then appropriately worked up. The residue obtained of the intermediate N-(4-chlorobenzene-sulphonyl)-thioxanthone-S-oximide (m.p. 192° C.; yield 60% of theory) can be recrystallized from acetonitrile. After saponification with concentrated sulphuric acid and recrystallization of the product from isopropanol, pure thioxanthone-S-oximide is obtained which melts at 168°–169° C. The saponification step proceeds with a yield of 83% of theory.

EXAMPLE 8

Phenoxathiine-S-oximide

VARIANT A 10.8 g. phenoxathiine-S-oxide are reacted with 10 g. tosyl azide and 4.5 g. copper powder in 350 ml. methanol in the manner described in Example 5, Variant A. After 1.5 and 3 hours, a further 5 g. tosyl azide and 4.5 g. copper powder are added. The reaction time is 6 hours. The residue obtained after working up is the intermediate N-(p-toluene-sulphonyl)-phenoxathiine-S-oximide which, after recrystallization from acetonitrile, melts at 170°–171° C. The yield is 60% of theory.

After saponification with concentrated sulphuric acid and recrystallization from benzene/diisopropyl ether, there is obtained pure phenoxathiine-S-oximide, which melts at 108°–109° C. The saponification step gives a yield of 80% of theory.

VARIANT B 20.8 g. phenoxathiine-S-imide mesitylene sulphonate are dissolved in 300 ml. glacial acetic acid and oxidised with 21.3 g sodium periodate in 300 ml. water. The reaction mixture is stirred for a further 24 hours at ambient temperature, then poured on to ice, rendered alkaline with aqueous sodium hydroxide solution and extracted with methylene chloride. After stripping off the solvent in a vacuum, the residue obtained is recrystallized from benzene/diisopropyl ether. Pure phenoxathiine-S-oximide is obtained in a yield of 86% of theory; m.p. 108°–109° C.

The phenoxathiine-S-imide-mesitylene sulphonate is prepared in the following manner:

5 g. phenoxathiine are stirred for 48 hours at ambient temperature with 6 g. mesitylene sulphonyl hydroxylamine in 50 ml. methylene chloride. The reaction mixture is subsequently mixed with a large amount of ether and the precipitate obtained is filtered off with suction. After recrystallization thereof from ethyl acetate/isopropanol, there is obtained phenoxathiine-S-imide mesitylene sulphonate in a yield of 57% of theory; m.p. 165° C.

Using the product of the above examples, the products of general formula I can be prepared.

Process "A" is, most simply, carried out by dissolving the starting materials of general formula (VI) in a dry solvent, for example, benzene, toluene, a xylene, tetrahydrofuran, dioxan or dimethyl sulphoxide, and, by the addition of a molar amount of sodium, potassium or sodium hydride at a temperature between about 20° C. and 100° C., converting them into the corresponding sulphoximide alkali metal salts. To the reaction mixture there is subsequently added a compound of general formula (VII) and the reaction mixture allowed to react at 50 to 150° C. for 30 minutes to 10 hours.

Methods "B" and "C" can be carried out by reacting the starting material of general formula (VI) in an appropriate solvent, for example chloroform, dichloromethane, benzene, toluene, a xylene, dioxan, tetrahydrofuran or acetone, with the addition of a hydrohalic acid acceptor, for example, triethylamine, pyridine or potassium carbonate, with a molar amount or an excess of a carboxylic acid chloride, preferably a chloride of an acid of general formula (VIII), or of a halocarbonic acid ester of general formula (IX), at ambient temperature for 1 to 20 hours. Carbamic acid halides are reacted in an analogous manner according to method "D".

The reaction according to "D" can take place in a solvent, for example, benzene, toluene, a xylene, dioxan, tetrahydrofuran or acetone, or in an excess of the isocyanate or isothiocyanate used of general formula (X) at a temperature of 20° to 140° C. for a period of 1 to 24 hours. If the free isocyanic or isothiocyanic acid is used, the reaction can be carried out with the addition of an inorganic or organic acid, preferably of acetic or trifluoroacetic acid.

If the compounds (I) possess a free basic amino group, they can be converted into pharmacologically compatible salts in the conventional manner, for example, by neutralization of the free base with pharmacologically compatible inorganic or organic acids, for example, hydrochloric acid, sulphuric acid, phosphoric acid, hydrobromic acid, acetic acid, lactic acid, citric acid, malic acid, salicylic acid, malonic acid, maleic acid or succinic acid.

The following examples are given for the purpose of illustrating the formation of the novel family of compounds encompassed by general formula I:

EXAMPLE 9

N-chloroacetyl-phenoxathiine-S-oximide 11.5 g. phenoxathiine-S-oximide and 7.6 g. triethylamine are dissolved in 150 cc. chloroform. While stirring and cooling, there is added dropwise a solution of 7.9 g. chloroacetyl chloride in 50 cc. chloroform. After having stirred the reaction mixture for 30 minutes at ambient temperature, it is mixed with water, acidified with dilute hydrochloric acid and the phases separated. The chloroform phase is washed with water, dried and evaporated. The crystalline residue is recrystallized from isopropanol, whereafter it melts at 137°–138° C.

EXAMPLE 10

N-(2-Diethylaminoethyl)-dibenzothiophene-S-oximide 13.4 g. dibenzothiophene-S-oximide are dissolved in 700 cc. anhydrous toluene, mixed portionwise with 3 g. sodium hydride (as a 50% oil suspension) and heated to 80° C. for 15 minutes. The sodium salt of the sulphoximide precipitates out in the form of a voluminous precipitate. 10 g. 2-diethylaminoethyl chloride are added dropwise to this suspension and the reaction mixture thereafter heated under reflux for 6 hours. After cooling, the reaction mixture is poured into water and the toluene phase separated off. This is washed with water, dried over anhydrous sodium sulphate and evaporated. The residue obtained is dissolved in ether and mixed with an ethereal solution of fumaric acid. The fumarate of N-(2-diethylaminoethyl)-dibenzothiophene-S-oximide precipitates out in the form of a colorless precipitate which is separated off and recrystallized from isopropanol; m.p. 170° C.

In an analogous manner, there is obtained N-(2-piperidino-ethyl)-dibenzothiophene-S-oximide from dibenzothiophene-S-oximide and 2-piperidinoethyl chloride. The oxalate thereof has a melting point of 216° C., after recrystallization from ethyl acetate.

EXAMPLE 11

N-(2-Diethylaminoethyl)-phenoxathiine-S-oximide

A solution of 9.3 g. phenoxathiine-S-oximide in 400 cc. anhydrous dioxan is mixed portionwise with an equimolar amount of sodium hydride and briefly heated to the boil, a voluminous precipitate of the sodium salt of the sulphoximide thereby being formed. 8 g. 2-diethylaminoethyl chloride is added dropwise to this suspension, followed by heating under reflux for 3 hours. Thereafter, the reaction mixture is evaporated in a vacuum, the residue obtained is taken up in dichloromethane and the organic phase is washed with water, dried over anhydrous sodium sulphate and evaporated. The residue is converted into the corresponding oxalate in the usual manner. There is obtained N-(2-diethylaminoethyl)-phenoxathiine-S-oximide oxalate which, after recrystallization from ethanol, melts at 163° C.

In an analogous manner, there is obtained N-(3-dimethylaminopropyl)-phenoxathiine-S-oximide dihydrochloride which, after recrystallization from ethyl acetate/isopropanol, melts at 186°–188° C.

EXAMPLE 12

N-(2-Diethylaminoethyl)-thioxanthene-S-oximide

In a manner analogous to that described in Example 11, by the reaction of thioxanthene-S-oximide with 2-diethylaminoethyl chloride, there is obtained N-(2-diethylaminoethyl)-thioxanthene-S-oximide dihydrochloride which, after recrystallization from isopropanol/ethanol, melts at 198° C.

EXAMPLE 13

N-(2-Diethylaminoethyl)-thianthrene-S-oximide

Diethylaminoethyl chloride is reacted with thianthrene-S-oximide in a manner analogous to that described in Example 11. There is obtained N-(2-diethylaminoethyl)-thianthrene-S-oximide which, after recrystallization from diisopropyl ether, melts at 100° C.

EXAMPLE 14

N-(2-Piperidinoethyl)-thioxanthone-S-oximide

Thioxanthone-S-oximide is reacted with 2-piperidino-ethyl chloride in a manner analogous to that described in Example 11. N-(2-piperidinoethyl)-thioxanthone-S-oximide hydrochloride is obtained which, after recrystallization from isopropanol, melts at 200° C.

The following compound is obtained in an analogous manner: N-(3-dimethylaminopropyl)-thioxanthone-S-oximide hydrochloride which, after recrystallization from isopropanol/methanol melts at 199°–210° C.

EXAMPLE 15

10-Methyl-phenothiazine-N-(2-diethylaminoethyl)-S-oximide

In a manner analogous to that described in Example 11, by the reaction of 10-methyl-phenothiazine-S-oximide with 2-diethylaminoethyl chloride, there is obtained 10-methyl-phenothiazine-N-(2-diethylaminoethyl)-S-oximide which, after recrystallization from diisopropyl ether/ethyl acetate, melts at 82°–83° C.

EXAMPLE 16

10-Acetyl-phenothiazine-N-(3-dimethylaminopropyl)-S-oximide 10-acetyl-phenothiazine-S-oximide is reacted with 3-dimethylaminopropyl chloride in a manner analogous to that described in Example 11. There is obtained 10-acetyl-phenothiazine-N-(3-dimethylaminopropyl)-S-oximide which, after recrystallization from ethyl acetate, melts at 149°–150° C.

In an analogous manner, there is obtained 10-acetyl-phenothiazine-N-(2-piperidinoethyl)-S-oximide which, after recrystallization from ethyl acetate, melts at 140° C.

EXAMPLE 17

Phenothiazine-N-(2-piperidinoethyl)-S-oximide

In a manner analogous to that described in Example 11, phenothiazine-S-oximide is reacted with 2-piperidinoethyl chloride. Phenothiazine-N-(2-piperidinoethyl)-S-oximide dihydrochloride is thus obtained which, after recrystallization from methanol/ether, melts, with decomposition, at 284° C.

EXAMPLE 18

N-(Diethylaminoacetyl)-phenoxathiine-S-oximide

A mixture of 14.8 g. N-chloroacetyl-phenoxathiine-S-oximide, 14.6 g. diethylamine and 250 cc. anhydrous ethanol is heated under reflux for 2 hours. Thereafter, the reaction mixture is evaporated in a vacuum and the residue is mixed with a dilute aqueous solution of sodium hydroxide and then extracted with chloroform. The extract is washed with water, dried over anhydrous sodium sulphate and evaporated. The crystalline residue is recrystallized from isopropanol. N-(diethylaminoacetyl)-phenoxathiine-S-oximide is obtained which melts at 112° C. The corresponding hydrochloride melts, with decomposition, at 213° C.

EXAMPLE 19

10-Methyl-phenothiazine-N-(3-diethylaminopropionyl)-S-oximide

10-Methyl-phenothiazine-N-(3-chloropropionyl)-S-oximide is reacted with diethylamine in a manner analogous to that described in Example 18. 10-methyl-phenothiazine-N-(3-diethylaminopropionyl)-S-oximide hydrochloride is obtained which, after recrystallization from isopropanol, melts at 197°–198° C.

The 10-methyl-phenothiazine-N-(3-chloropropionyl)-S-oximide used as starting material is obtained by the reaction of 10-methylphenothiazine-S-oximide with 3-chloropropionyl chloride. After recrystallisation from ethyl-acetate, it melts at 156°–158° C.

EXAMPLE 20

10-Acetyl-phenothiazine-N-(ethoxycarbonyl)-S-oximide 13 g. ethyl chloroformate are added dropwise to a solution of 13.6 g. 10-acetyl-phenothiazine-S-oximide and 5.1 g. triethylamine in 150 cc. chloroform and the reaction mixture thereafter heated under reflux for 10 hours. After cooling, the chloroform phase is washed with water, dried over anhydrous sodium sulphate and evaporated. The residue is recrystallized from chloroform/methanol. 10-Acetyl-phenothiazine-N-(ethoxycarbonyl)-S-oximide is obtained; m.p. 187°–188° C.

EXAMPLE 21

N-Carbamoyl-dibenzothiophene-S-oximide 12.9 g. dibenzothiophene-S-oximide are dissolved in 300 cc. 80% acetic acid and mixed with a solution of 9.7 g. potassium cyanate in 20 cc. water. The solution is stirred for 2 hours at 80° C., a precipitate thereby being obtained. This is filtered off with suction, washed with water and recrystallized from dimethyl formamide. N-Carbamoyl-dibenzothiophene-S-oximide is obtained; m.p. 266°–267° C.

EXAMPLE 22

N-(n-Butyl-carbamoyl)-dibenzothiophene-S-oximide 10.8 g. dibenzothiophene-S-oximide, together with 5.5 g. n-butyl isocyanate, are heated under reflux for 20 hours in 250 cc. anhydrous toluene. Thereafter, the reaction mixture is evaporated in a vacuum and the residue obtained is recrystallized from ethyl acetate. N-(n-Butyl-carbamoyl)-dibenzothiophene-S-oximide is obtained; m.p. 121°–122° C.

The following compounds are obtained in an analogous manner by the reaction of the appropriate S-oximides with the appropriate isocyanates or isothiocyanates:

N-(n-butyl-carbamoyl)-phenoxathiine-S-oximide; m.p. 139° C. (recrystallized from ethyl acetate);

N-(n-butyl-carbamoyl)-thianthrene-S-oximide; m.p. 146° C. (recrystallized from ethyl acetate);

10-acetyl-phenothiazine-N-(cyclohexyl-carbamoyl)-S-oximide; m.p. 221°–222° C. (recrystallized from chloroform/ether);

phenothiazine-N-(cyclohexyl-carbamoyl)-S-oximide; m.p. 251° – 252° C. (recrystallized from ethanol);

10-methyl-phenothiazine-N-(allyl-thiocarbamoyl)-S-oximide; m.p. 187° – 188° C. (recrystallized from chloroform/ether); and 10-methyl-phenothiazine-N-(p-toluene-sulphonyl-carbamoyl)-S-oximide; m.p. 273°–274° C. (decomp.) (recrystallized from dimethyl formamide/ethanol).

10-methyl-phenothiazine-S-oximide:

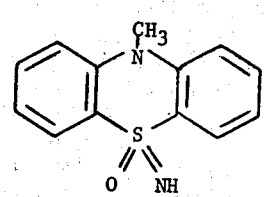

10-acetyl-phenothiazine-S-oximide:

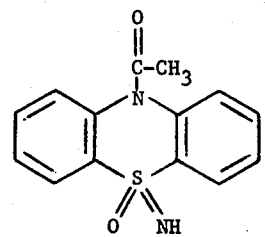

Phenothiazine-S-oximide:

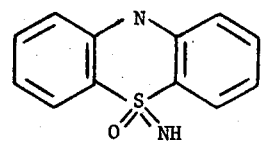

Dibenzothiophene-S-oximide:

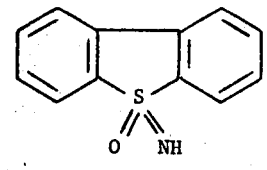

Thioxanthene-S-oximide:

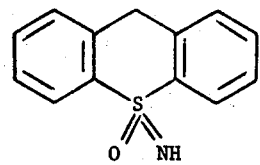

Thioxanthone-S-oximide:

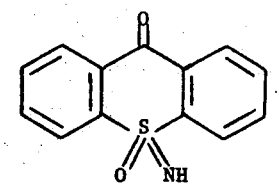

Phenoxathiine-S-oximide:

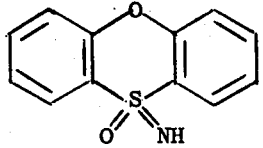

Thianthrene-S-oximide:

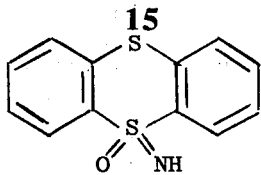

The compounds of the present invention include those having the following structural formula:

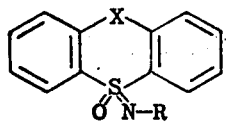

| Example | X | R | Salt | Melting point (°C) |
|---|---|---|---|---|
| 10 | — | $CH_2-CH_2-N(C_2H_5)_2$ | fumarate | 170 |
| 10b | — | $CH_2-CH_2-N\langle\rangle$ | oxalate | 216 |
| 11 | O | $CH_2-CH_2-N(C_2H_5)_2$ | oxalate | 163 |
| 11b | O | $CH_2-CH_2-CH_2-N(CH_3)_2$ | dihydrochloride | 186–8 |
| 12 | $CH_2$ | $CH_2-CH_2-N(C_2H_5)_2$ | dihydrochloride | 198 |
| 13 | S | $CH_2-CH_2-N(C_2H_5)_2$ | — | 100 |
| 14 | CO | $CH_2-CH_2-N\langle\rangle$ | hydrochloride | 200 |
| 14b | CO | $CH_2-CH_2-CH_2-N(CH_3)_2$ | hydrochloride | 199–201 |
| 15 | $N-CH_3$ | $CH_2-CH_2-N(C_2H_5)_2$ | — | 82–83 |
| 16 | $N-CO-CH_3$ | $CH_2-CH_2-CH_2-N(CH_3)_2$ | — | 149–150 |
| 16b | $N-CO-CH_3$ | $CH_2-CH_2-N\langle\rangle$ | — | 140 |
| 17 | NH | $CH_2-CH_2-N\langle\rangle$ | hydrochloride | 284 |
| 18 | O | $CO-CH_2-N(C_2H_5)_2$ | hydrochloride | 213 |
| 19 | $N-CH_3$ | $CO-CH_2-CH_2-N(C_2H_5)_2$ | hydrochloride | 197–8 |
| 20 | $N-CO-CH_3$ | $CO-OC_2H_5$ | — | 187–8 |
| 21 | — | $CO-NH_2$ | — | 266–7 |
| 22a | — | $CO-NH-C_4H_9$ | — | 121–2 |
| 22b | O | $CO-NH-C_4H_9$ | — | 139 |
| 22c | S | $CO-NH-C_4H_9$ | — | 146 |
| 22d | $N-CO-CH_3$ | $CO-NH-C_6H_{11}$ | — | 221–2 |
| 22e | NH | $CO-NH-C_6H_{11}$ | — | 251–2 |
| 22f | $N-CH_3$ | $CS-NH-CH_2-CH=CH_2$ | — | 187–8 |
| 22g | $N-CH_3$ | $CO-NH-SO_2-C_6H_4CH_3(p)$ | — | 273–4 |

In a series of conventional experiments to show the pharmaceutical utility of the compounds of this invention, the following examplary results were obtained:

EXAMPLE 15

$LD_{50}$ is about 600 mg/kg i.g.
100 mg/kg when given i.g. shows antiphlogistic and analgesic properties in mammals.

EXAMPLE 19

$LD_{50}$ is greater than 1600 mg/kg i.g.
250 mg/kg produces diuresis in mammals.

EXAMPLE 16

$LD_{50}$ is about 200 mg/kg s.c.
15 mg/kg when given s.c. has a sedative effect equivalent to 40 mg/kg of methaqualone.

EXAMPLE 17

$LD_{50}$ is about 300 mg/kg s.c.
50–100 mg/kg shows analgesic and antiphlogistic properties in mammals.
200 mg/kg i.g. has an antitussive effect equivalent to 150 mg/kg i.g. of codeine.
100 mg/kg s.c. has an antitussive effect corresponding to about 50 mg/kg s.c. of codeine.
100 mg/kg s.c. shows antisecretory effects in the shay rat screening tests.

EXAMPLE 21

$LD_{50}$ is between 50 and 400 mg/kg s.c.
25 mg/kg s.c. shows sedative effects.

The compounds (I) and the salts thereof can be administered enterally or parenterally in admixture with solid or liquid pharmaceutical diluents or carriers. As injection medium, there is preferably used water which contains the conventional additives for injection solutions, for example stabilizing agents, solubilizing agents or buffers. Additives of this type include, for example, tartrate and citrate buffers, ethanol, complex-forming agents, for example, ethylenediamine-tetraacetic acid and the non-toxic salts thereof and high molecular weight polymers, for example liquid polyethylene oxide, for viscosity regulation. Solid carrier materials include, for example, starch, lactose, mannitol, methylcellulose, talc, highly-dispersed silicic acids, high molecular weight fatty acids, for example stearic acid, gelatine, agar-agar, calcium phosphate, magnesium stearate, animal and vegetable fats and solid high molecular weight polymers, for example, polyethylene glycols; compositions suitable for oral administration can, if desired, contain flavoring and sweetening agents.

The dosage of the compounds according to the present invention depends upon the nature and severity of the disease to be treated. The oral individual dose is usually 20 to 200 mg., the intravenous individual dose is usually 1 to 20 mg. and the subcutaneous individual dose is usually 1 to 100 mg.

We claim:

1. A tricyclic sulphoximide of the formula:

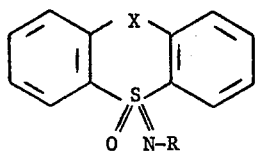

wherein X is N—$CH_3$, N—CO—$CH_3$, or N—H; wherein R is $CH_2$—$CH_2$—$N(C_2H_5)_2$, $CH_2$—$CH_2$—$CH_2$—$N(CH_3)_2$,

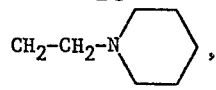

CO—$CH_2$—$CH_2$—$N(C_2H_5)_2$, CO—O—$C_2H_5$, CO—NH—$C_6H_{11}$, CS—NH—$CH_2$—CH=$CH_2$, or CO—NH—$SO_2$—$C_6H_4CH_3(p)$.

2. The sulphoximide of claim 1 which is 10-Methyl-phenothiazine-N-(2-diethylaminoethyl)-S-oximide.

3. The sulphoximide of claim 1 which is 10-Acetyl-phenothiazine-N-(3-dimethylaminopropyl)-S-oximide.

4. The sulphoximide of claim 1 which is 10-Acetyl-phenothiazine-N-(2-piperidinoethyl)-S-oximide.

5. The sulphoximide of claim 1 which is Phenothiazine-N-(2-piperidinoethyl)-S-oximide.

6. The sulphoximide of claim 1 which is 10-Methyl-phenothiazine-N-(3-diethylaminopropionyl)-S-oximide.

7. The sulphoximide of claim 1 which is 10-Acetyl-phenothiazine-N-(ethoxycarbonyl)-S-oximide.

8. The sulphoximide of claim 1 which is 10-Acetyl-phenothiazine-N-(cyclohexylcarbamoyl)-S-oximide.

9. The sulphoximide of claim 1 which is Phenothiazine-N-(cyclohexylcarbamoyl)-S-oximide.

10. The sulphoximide of claim 1 which is 10-Methyl-phenothiazine-N-(allylthiocarbamoyl)-S-oximide.

11. The sulphoximide of claim 1 which is 10-Methyl-phenothiazine-N-(p-toluenesulphonyl-carbamoyl)-S-oximide.

* * * * *